United States Patent
Gass et al.

(10) Patent No.: US 10,866,353 B2
(45) Date of Patent: Dec. 15, 2020

(54) SYSTEMS, METHODS AND APPARATUS FOR ILLUMINATING EDGE PORTIONS OF A FACE OF AN ELECTRONIC DEVICE DISPLAY LENS

(71) Applicant: ASCENSIA DIABETES CARE HOLDINGS AG, Basel (CH)

(72) Inventors: Jennifer L. Gass, Tarrytown, NY (US); Eugene R. Prais, West Milford, NJ (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

(21) Appl. No.: 16/465,569

(22) PCT Filed: Nov. 27, 2017

(86) PCT No.: PCT/EP2017/080491
§ 371 (c)(1),
(2) Date: May 30, 2019

(87) PCT Pub. No.: WO2018/099849
PCT Pub. Date: Jun. 7, 2018

(65) Prior Publication Data
US 2019/0293859 A1 Sep. 26, 2019

Related U.S. Application Data

(60) Provisional application No. 62/429,725, filed on Dec. 2, 2016.

(51) Int. Cl.
*G02B 6/00* (2006.01)
*F21V 8/00* (2006.01)
(Continued)

(52) U.S. Cl.
CPC .......... *G02B 6/0046* (2013.01); *A61B 5/742* (2013.01); *G02B 6/008* (2013.01); *G02B 6/0033* (2013.01);
(Continued)

(58) Field of Classification Search
CPC .......................... G02B 6/0046; G02B 6/0048
(Continued)

(56) References Cited

U.S. PATENT DOCUMENTS 5,453,855 A * 9/1995 Nakamura ........... G02B 6/0051
349/58
5,975,711 A 11/1999 Parker et al.
(Continued)

FOREIGN PATENT DOCUMENTS

DE 19918053 11/2000
DE 102008006421 A1 7/2009
(Continued)

OTHER PUBLICATIONS

International Preliminary Report on Patentability of International Application No. PCT/EP2017/080491 dated Jun. 13, 2019.
(Continued)

*Primary Examiner* — Christopher M Raabe
(74) *Attorney, Agent, or Firm* — Dugan & Dugan, PC

(57) ABSTRACT

Embodiments provide systems, methods and apparatus for illuminating a portion of the face of a display lens proximate to and along one or more edges of the display lens. The display lens includes a transparent lens having four edges and a face surface. At least one edge includes an angle relative to the face surface configured to reflect light in the lens out of the face surface. Numerous other aspects are provided.

20 Claims, 7 Drawing Sheets

(51) Int. Cl.
*A61B 5/00* (2006.01)
*A61B 5/145* (2006.01)

(52) U.S. Cl.
CPC ......... *G02B 6/0035* (2013.01); *G02B 6/0045* (2013.01); *G02B 6/0055* (2013.01); *A61B 5/14532* (2013.01); *G02B 6/0013* (2013.01); *G02B 6/0058* (2013.01); *G02B 6/0061* (2013.01)

(58) Field of Classification Search
USPC ........................................................ 362/611
See application file for complete search history.

(56) References Cited

U.S. PATENT DOCUMENTS

| | | | |
|---|---|---|---|
| 7,034,799 | B2 | 4/2006 | Lee |
| 7,963,689 | B2 | 6/2011 | Lee |
| 9,071,676 | B2 | 6/2015 | Prais |
| 9,983,341 | B2 | 5/2018 | Prais |
| 2004/0052066 | A1 | 3/2004 | Funamoto et al. |
| 2005/0259939 | A1 | 11/2005 | Rinko |
| 2006/0274548 | A1 | 12/2006 | Chang et al. |
| 2007/0253216 | A1 | 11/2007 | Fisher |
| 2008/0278460 | A1* | 11/2008 | Arnett .................. G06F 3/0428 345/175 |
| 2009/0059618 | A1 | 3/2009 | Onikiri |
| 2009/0257712 | A1 | 10/2009 | Van Gorkom et al. |
| 2010/0053229 | A1* | 3/2010 | Krijn .................. G02B 6/0038 345/690 |
| 2010/0317951 | A1 | 12/2010 | Rutkowski et al. |
| 2011/0090694 | A1* | 4/2011 | Hardacker ............... H04N 5/64 362/257 |
| 2012/0201048 | A1 | 8/2012 | Prais |
| 2015/0253483 | A1 | 9/2015 | Prais |
| 2017/0234858 | A1* | 8/2017 | Depa .................. A61B 5/14532 436/165 |
| 2018/0275332 | A1 | 9/2018 | Prais |

FOREIGN PATENT DOCUMENTS

| | | |
|---|---|---|
| EP | 1574780 A1 | 9/2005 |
| EP | 02023193 A1 | 2/2009 |
| EP | 2025994 | 2/2009 |
| JP | 2001-358816 | 12/2001 |
| JP | 2003-302635 | 10/2003 |
| WO | WO07002476 A2 | 1/2007 |
| WO | WO 2012/043406 | 4/2012 |

OTHER PUBLICATIONS

International Search Report and Written Opinion of International Application No. PCT/US2012/023331 (BHDD/025/WO) dated Sep. 14, 2012.
International Preliminary Report on Patentability and Written Opinion of International Application No. PCT/US2012/023331 (BHDD/025/WO) dated Aug. 15, 2013.
European Search Report of European Application No. 12707678.4 (BHDD-025-PCT-EP) dated Oct. 25, 2018.
International Search Report and Written Opinion of International Application No. PCT/EP2017/080491 dated Mar. 5, 2018.
Chinese Search Report of Chinese Application No. 201780074909.3 dated Mar. 31, 2020.

\* cited by examiner

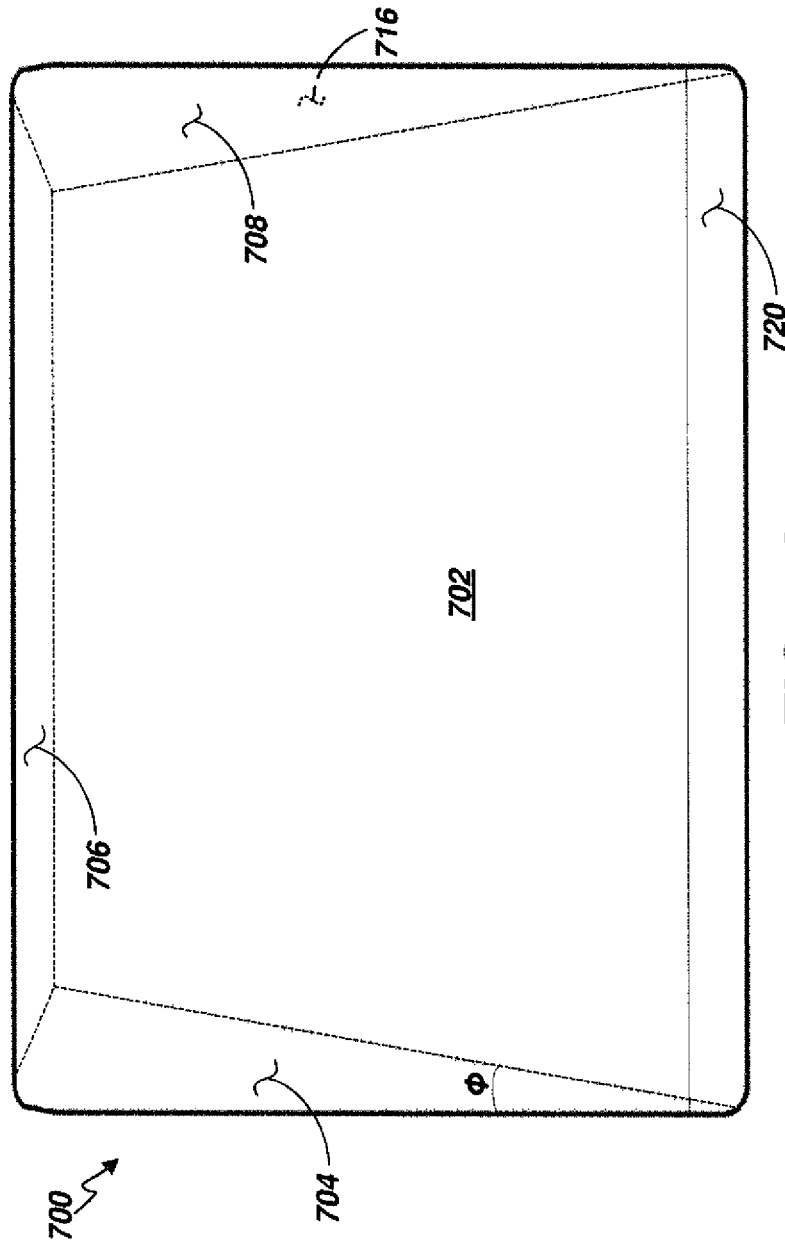
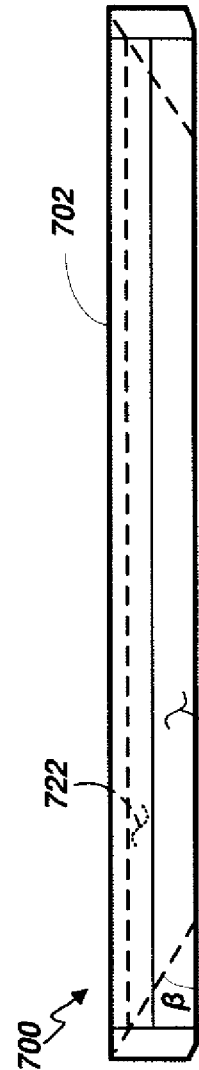
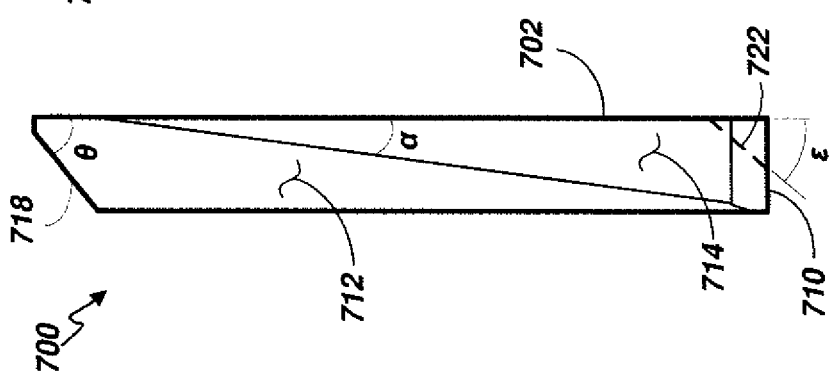
FIG. 7A
FIG. 7B
FIG. 7C

SYSTEMS, METHODS AND APPARATUS FOR ILLUMINATING EDGE PORTIONS OF A FACE OF AN ELECTRONIC DEVICE DISPLAY LENS

CROSS REFERENCE TO RELATED APPLICATION

This claims priority to U.S. Provisional Patent Application No. 62/429,725, filed Dec. 2, 2016, which is hereby incorporated by reference herein in its entirety for all purposes.

FIELD

Embodiments of the invention relate to display lenses of electronic devices such as analyte monitoring devices (e.g., blood glucose meters), and more specifically to systems, methods and apparatus that illuminate a portion of the face of a display lens proximate to and along one or more edges of the display lens.

BACKGROUND

Electronic devices with display screens that are designed to be as inexpensive as possible typically do not have color displays. Instead, "black and white" or monochrome liquid crystal displays (LCDs) are used. However, contrasting color enhances usability and helps more clearly convey information. Previous attempts to include color in an inexpensive electronic device's interface have relied upon discrete colored LEDs (light emitting diodes) that are usually separate from the information display screen. Unfortunately though, users may not readily associate the colored LEDs with the information being presented on the display. Thus, what is needed are improved methods and apparatus for inexpensively facilitating and integrating contrasting color into a display screen of an electronic device.

SUMMARY

In some embodiments, a method for illuminating a portion of the face of a display lens proximate to and along one or more edges of the display lens is provided. The method includes providing a display lens having an angled edge coated with a reflective material; directing light from a light source at an edge of the display lens opposite the angled edge; and transmitting the light through the display lens to reflect off the angled edge and out an edge portion of a face of the display lens.

In other embodiments, a display lens for an electronic device is provided. The display lens includes a transparent lens having four edges and a face surface. At least one edge includes an angle relative to the face surface configured to reflect light in the lens out of the face surface.

In still other embodiments, an analyte monitoring device is provided. The analyte monitoring device includes an electronic display including a display lens; and a light source disposed adjacent the display lens and configured to illuminate a first edge of the display lens. The display lens includes a transparent lens having four edges and a face surface. A second edge includes an angle relative to the face surface configured to reflect light in the lens out of the face surface.

Numerous other aspects are provided in accordance with these and other aspects of the invention. Other features and aspects of the invention will become more fully apparent from the following detailed description, the appended claims, and the accompanying drawings.

BRIEF DESCRIPTION OF THE DRAWINGS

FIGS. 7A to 7C illustrate front face, bottom side edge, and left side edge views, respectively, of an example of a display lens according to embodiments of the invention.

DESCRIPTION

Figure 1:
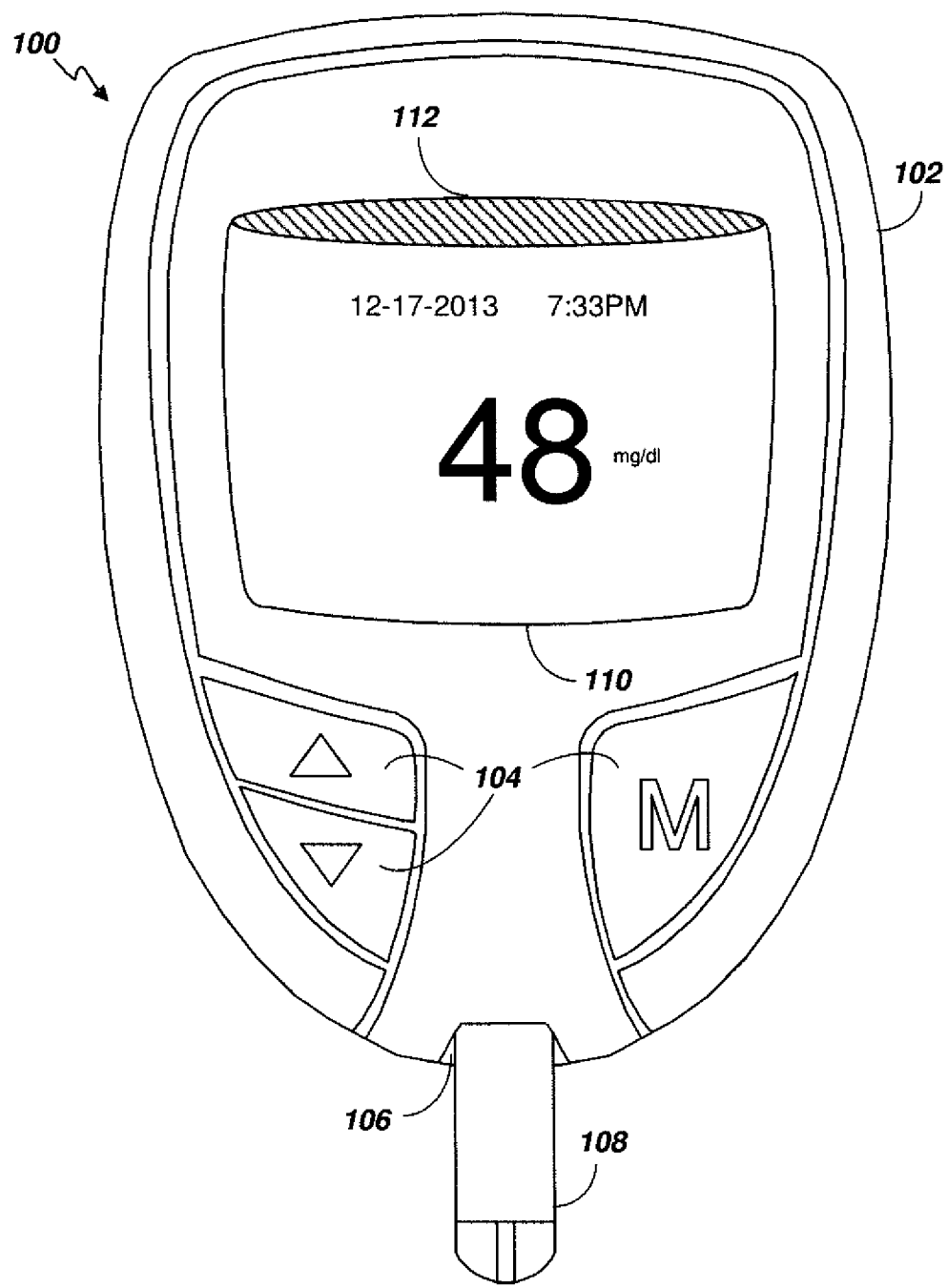
FIG. 1 illustrates a diagram depicting an example electronic device (e.g., an analyte monitoring device, such as a blood glucose meter) with a top front face edge portion of the display lens illuminated according to embodiments of the invention.

For the purposes of promoting an understanding of the principles of embodiments of the invention, reference will now be made to the examples illustrated in the drawings and specific language will be used to describe the same. It will nevertheless be understood that no limitation of the scope of the invention is thereby intended, and any alterations and further modifications in the illustrated embodiments, and any further applications of the principles of the invention as illustrated therein as would normally occur to one skilled in the art to which the invention relates are contemplated herein.

Embodiments of the invention provide systems, apparatus, and methods for a display lens that allows color and light to be easily and inexpensively incorporated into the display of an electronic device such as an analyte monitoring device (e.g., a blood glucose meter). Instead of using discrete LEDs that are separate from the display screen and which may not be readily associated with the information being conveyed on the display screen, embodiments of the invention provide an inexpensive and cost effective means to project colored light from the edge portions of the front face of a display screen of an electronic device such as an analyte monitoring device (e.g., a blood glucose meter (BGM)). So for example, if the BGM is displaying a numeric value representing a dangerously high or low blood glucose level (e.g., above or below a predefined threshold), the edge portions of the front face of the display can project red light indicating the urgent severity and seriousness of the reading by framing the display in red. If the numeric value is within a desired target range, a green light can be projected from the edge portions of the front face of the display indicating all is well. If the numeric value is outside of the target range but not quite into a critical or immediately dangerous range, a yellow light can be projected from the edge portions of the front face of the display indicating the user should be cautious. The example colors mentioned above are merely illustrative of a potential arrangement. It should be understood that numerous other colors and meanings can be assigned or associated with various values or other information being presented on the display screen.

Embodiments of the invention provide a screen display lens with angled or chamfered edges that are arranged to reflect light directed into a side edge of the display lens out the front face of the display lens along one or more edge portions of the front face. In some embodiments, the angled edges can include a reflective film or coating to help facilitate the reflection of the light. In some embodiments, a light source such as a tri-color LED or multiple single color LEDs can be used to illuminate the display. In some embodiments, the color of the light can be selected for display based upon information (e.g., numerical values such as blood glucose level) indicating, for example, an urgent condition such as a blood glucose level exceeding a critical high threshold (e.g., hyperglycemic) value or dropping below a critical low threshold (e.g., hypoglycemic) value. Different colors can be used to indicate different threshold value crossings or statuses. Other colors can be used to indicate that the displayed value is within an acceptable or desired range.

Embodiments of the invention are depicted in the example system 100 illustrated in FIG. 1. In some embodiments, an electronic device such as an analyte monitoring device (e.g., a blood glucose meter 102) can include a plurality of input buttons 104, a port 106 adapted to receive a blood glucose sensor strip 108, and a display screen 110 for displaying information to a user. The display screen 110 can include an edge portion 112 that is adapted to project colored light out of the front face of the display screen 110. The display screen 110 also includes conventional electronics (e.g., LCD circuitry, processor, memory, etc.) to generate information displays such as text and graphics.

Figure 2:
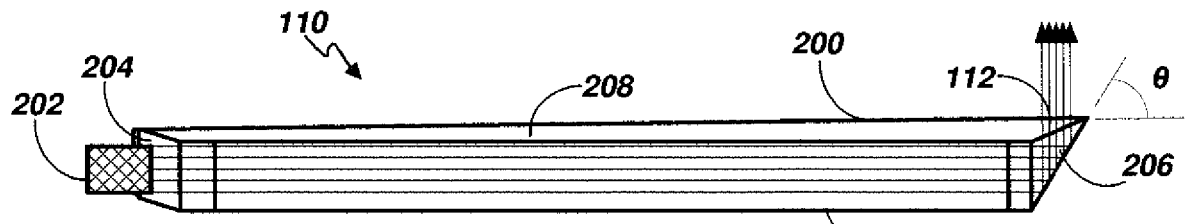
FIG. 2 illustrates a side cross-sectional view of a display lens with a top front face edge portion of the display illuminated according to embodiments of the invention.
Figure 3:
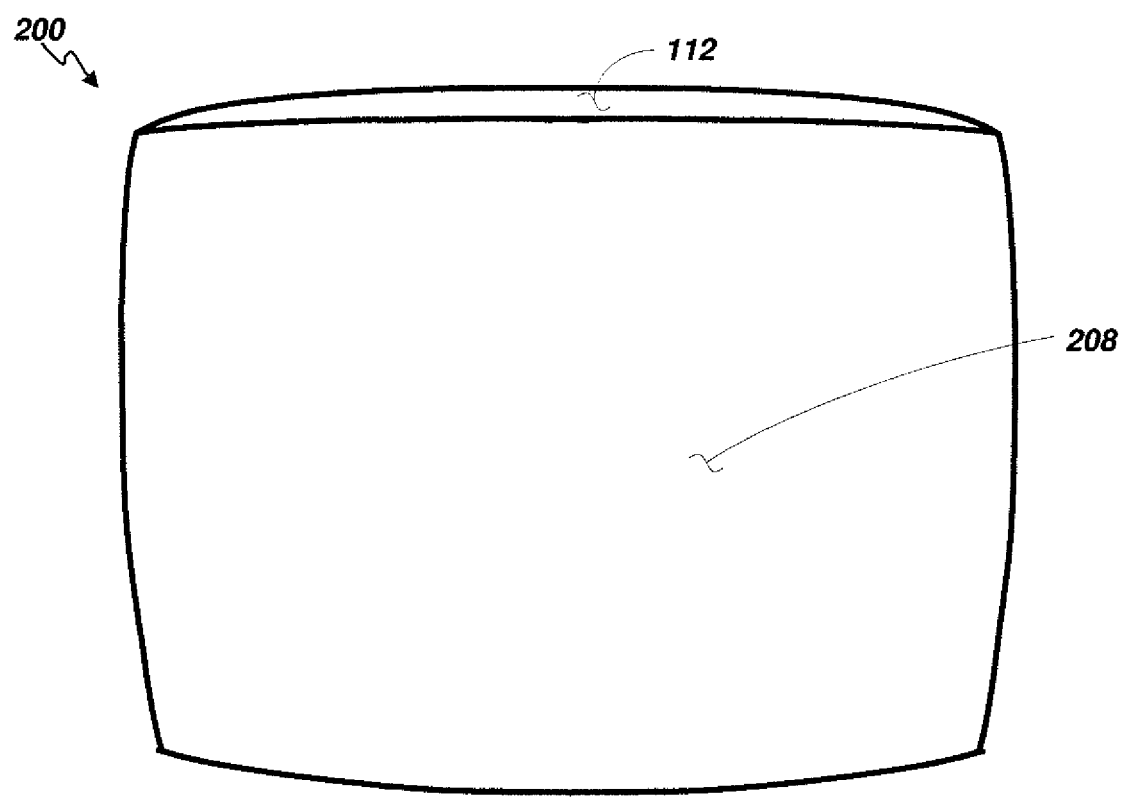
FIG. 3 illustrates a diagram depicting a front face view of an example of a display lens according to embodiments of the invention.
Figure 4:
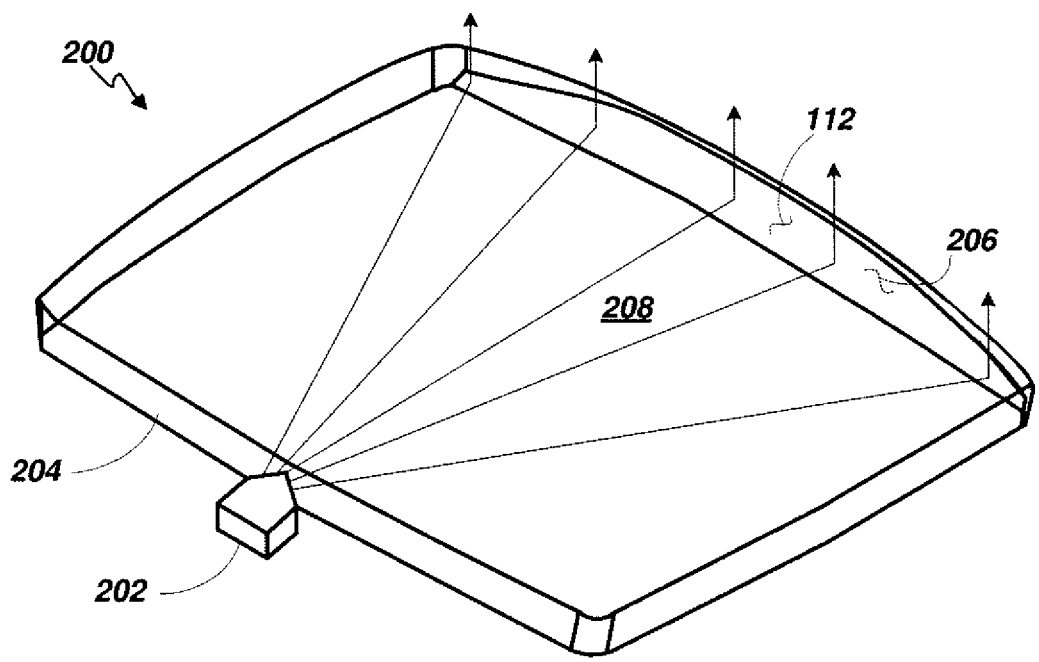
FIG. 4 illustrates an isometric view depicting an example of a display lens according to embodiments of the invention.

FIG. 2 is a center cross-sectional view of a display lens 200 of the display screen 110 of the analyte monitoring device (e.g., a blood glucose meter 102) of FIG. 1. FIG. 3 is a magnified plan view of the example display lens 200, and FIG. 4 is an isometric view of the same display lens 200. The display lens 200 can be a transparent glass or plastic protective cover for underlying LCD circuitry. Other transparent materials can be used for the display lens 200. In some embodiments, touch screen and/or haptic capabilities can be implemented with the display lens 200.

As shown in FIGS. 2 and 4, a light source 202 directs colored light (e.g., light rays represented as dotted lines in FIG. 4) into a side edge 204 of the display lens 200. The light travels within the display lens 200 which acts as a light guide containing the light within the display lens 200 until the light strikes the angled side edge 206 of the display lens 200. In some embodiments, a single light source 202 as shown in FIG. 4 is positioned in the center of the side edge 204 and light fans out from the light source 202. In other embodiments, multiple light sources disposed alongside edge 204 can be used.

As illustrated by the multiple arrows representing light rays in FIGS. 2 and 4, the angled side edge 206 (e.g., the side edge that is shown reflecting the light rays upward) is configured to reflect the light out of the edge portion 112 of the front face surface 208 of the display lens 200. In some embodiments, the angled side edge 206 is coated with a film or layer of reflective material such as aluminum, silver, or other similar material to enhance the reflection of the light. The angle θ of the angled side edge 206 relative to the front face surface 208 can be approximately forty-five degrees but can range from approximately thirty degrees to approximately sixty degrees. Other angles are possible. The angle of the angled side edge 206 can be formed by cutting a corner off of the display lens 200 so that a beveled edge is formed.

In some embodiments, the angled side edge 206 can be curved such that the bevel of the edge is either convex or concave. In addition, as most clearly seen in FIGS. 3 and 4, the angle of the angled side edge 206 can vary from the corner of the display lens 200 to the center of the display lens 200 such that the illuminated edge portion 112 has a crescent shape. Other shapes are possible. For example, the angled side edge 206 can be beveled to have an oval shape. In some embodiments, a reflective coating can be applied to only a portion of the angled side edge 206 so that any desired shape of light can be reflected out of the edge portion 112 of the front face surface 208 of the display lens 200.

In some embodiments, the display lens 200 can be curved in the longitudinal dimension, lateral dimension, or both. The curves can be concave, convex, and/or compound. In some embodiments, an angled cut can be made into either or both of the front face surface 208 and the back surface 210 of the display lens 200 to facilitate reflecting light out of any desired portion of the display lens 200. For example, if it is desired to be able to call attention to a numerical value displayed in the center of the display 110 with flashing red light underlining the numerical value, an angled cut at approximately forty-five degrees into the back surface 210 of the display lens 200 can be made at a location below (e.g., underlining) where the numerical value will be displayed. Reflective coating can be applied to the cut surface. In such embodiments, light moving laterally through the display lens 200 will be reflected upwards out of the front face surface 208 by the angled cut.

In some embodiments, the front face surface 208 and the back surface 210 of the display lens 200 are coated with an anti-reflective material such as magnesium fluoride that only allows light with an angle of incidence less than approximately sixty degrees to escape the display lens 200. In some embodiments, light is trapped within the display lens using a coating on the surfaces that only lets light escape at an angle of incidence to the surface greater than approximately sixty degrees and less than approximately 120 degrees.

Turning now to FIGS. 5A to 5C and FIG. 6, another embodiment of a display lens 500 is depicted. FIGS. 5A to 5C and 6 are front face, bottom side edge, left side edge, and isometric views, respectively, of an example of a display lens 500 that can reflect light out of the front face 502 along three edge portions: the left side edge portion 504, the top edge portion 506, and the right side edge portion 508.

Note that although terms such as top, left, right, and bottom are used throughout the specification and claims, these terms are merely intended to clarify the relative positions of features of the embodiments and are not intended as absolute positions. Thus, in alternative embodiments, the relative positions can be reversed or rotated as practicable. For example, one of ordinary skill would understand that light can be introduced into the display lens from any side edge (e.g., top, bottom, left, or right) of the display lens as long as the other side edges are appropriately angled relative to the edge in which the light enters the display lens.

Figure 5A:
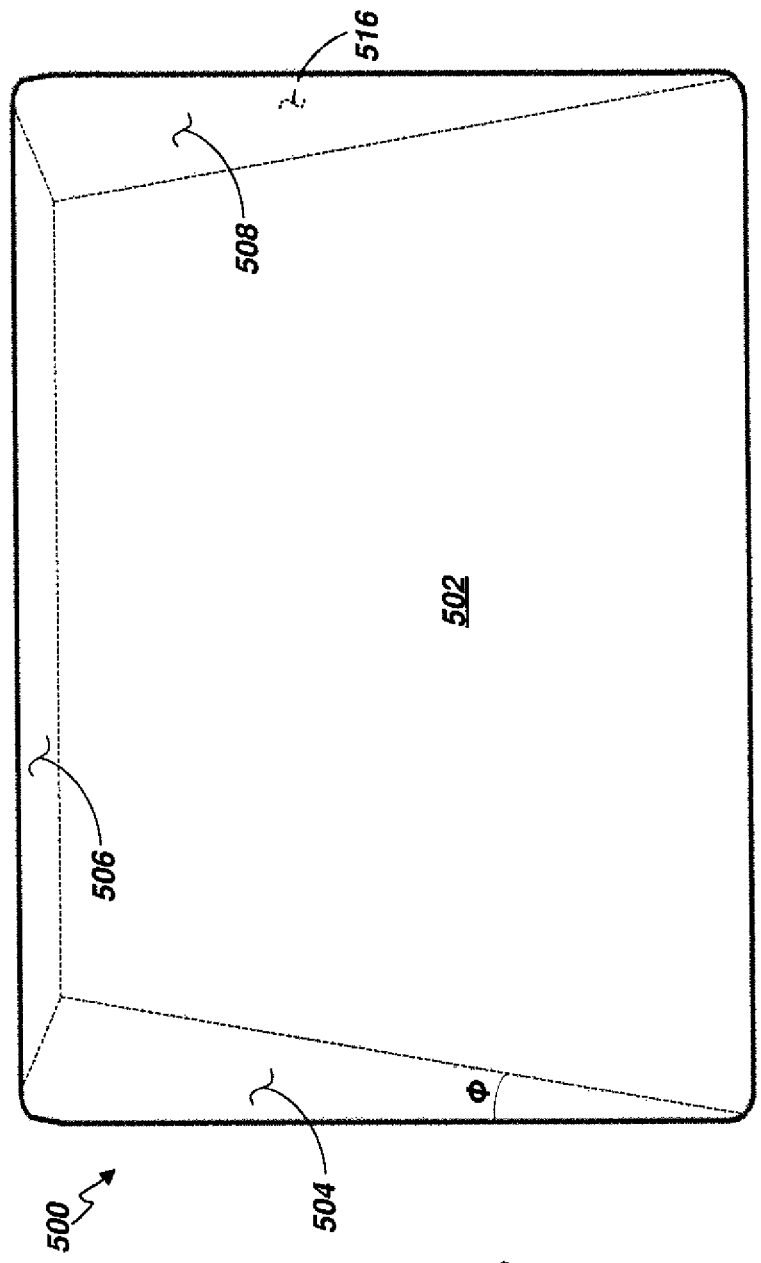
FIGS. 5A to 5C illustrate front face, bottom side edge, and left side edge views, respectively, of an example of a display lens according to embodiments of the invention.
Figure 5B:
Figure 5C:
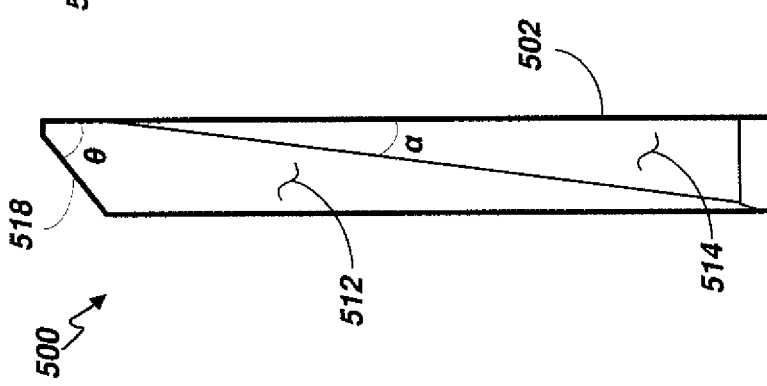
Figure 6:
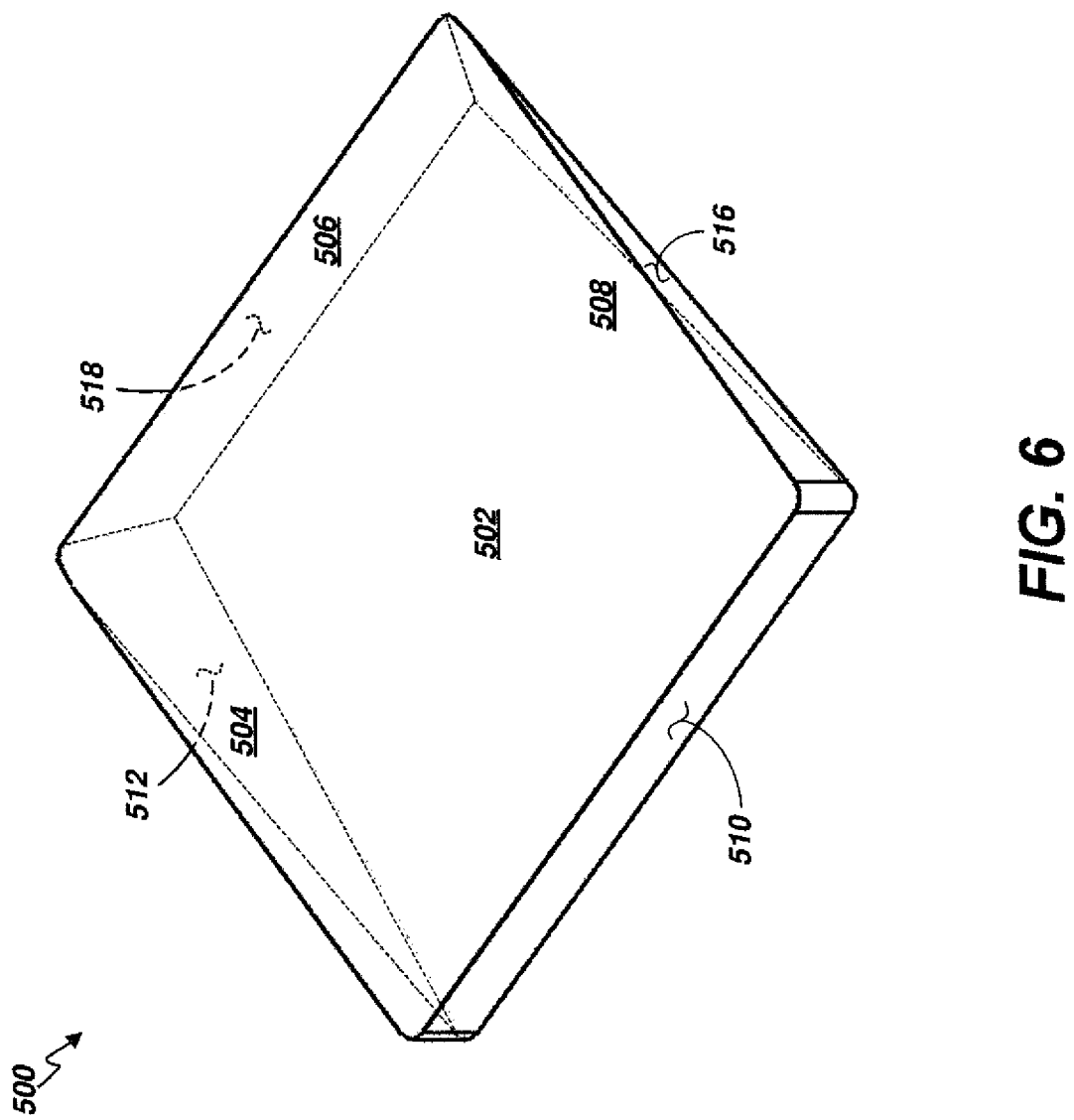
FIG. 6 illustrates an isometric view depicting the example display lens of FIGS. 5A to 5C according to embodiments of the invention.

In some embodiments, light enters the bottom side edge 510 from a light source (not shown but see light source 202 of FIG. 4 for a similar example) and is reflected out of the front face 502. For example, the light is reflected by the angled left side edge 512 out of the left side edge portion 504 of the front face 502. Note that as shown in FIGS. 5B and 5C, the angled left side edge 512 is angled relative to the front face 502 as indicated by angle α and angle β. In some embodiments, angle α can be dependent on the thickness and length of the lens. For example, in some embodiments, $$\alpha = \tan^{-1}\left(\frac{t}{l}\right)$$

where t is the lens thickness and l is the length of the front face 502 from the bottom side edge 510 to the top side edge 518. In some embodiments, angle β can be approximately forty-five degrees or in some embodiments, in the range of approximately thirty degrees to approximately sixty degrees. Other angles are possible. Note also that left side edge 514 is approximately perpendicular with the front face 502 of the display lens 500 and thus does not reflect light out of the front face 502 but can reflect light back into the display lens 500.

In addition to being angled relative to the front face 502, the angled left side edge 512 also angles inward going from the bottom side edge 510 to the top side edge 518 at an angle Φ relative to left side edge 514. In some embodiments, angle Φ can be approximately ten degrees or in some embodiments, in the range of approximately five degrees to approximately twelve degrees. Other angles are possible. Thus, angled left side edge 512 is disposed at a compound angle that allows light coming from bottom side edge 510 generally directed toward top side edge 518 to be reflected out the left side edge portion 504 of the front face 502.

Likewise, angled right side edge 516 mirrors angled left side edge 512 and is disposed at a compound angle that allows light coming from bottom side edge 510 generally directed toward top side edge 518 to be reflected out the right side edge portion 508 of the front face 502.

Angled top side edge 518 reflects light out top edge portion 506 of the front face 502. As shown in FIG. 5C, the angled top side edge 518 is angled relative to the front face 502 as indicated by angle θ. In some embodiments, angle θ can be approximately forty-five degrees or in some embodiments, in the range of approximately thirty degrees to approximately sixty degrees. Other angles are possible.

Turning now to FIGS. 7A to 7C and FIG. 8, another embodiment of a display lens 700 is depicted. FIGS. 7A to 7C and 8 are front face, bottom side edge, left side edge, and isometric views, respectively, of an example of a display lens 700 that can reflect light out of the front face 702 along four edge portions: the left side edge portion 704, the top edge portion 706, the right side edge portion 708, and the bottom edge portion 720.

Light enters the bottom side edge 710 from a light source (not shown but see light source 202 of FIG. 4 for a similar example) and is reflected out of the front face 702. For example, the light is reflected by the angled left side edge 712 out of the left side edge portion 704 of the front face 702. Note that as shown in FIGS. 7B and 7C, the angled left side edge 712 is angled relative to the front face 702 as indicated by angle α and angle β. In some embodiments, angle α can be dependent on the thickness and length of the lens. For example, in some embodiments, $$\alpha = \tan^{-1}\left(\frac{t}{l}\right)$$

where t is the lens thickness and l is the length of the front face 702 from the bottom side edge 510 to the top side edge 718. In some embodiments, angle β can be approximately forty-five degrees or in some embodiments, in the range of approximately thirty degrees to approximately sixty degrees. Other angles are possible. Note also that left side edge 714 is approximately perpendicular with the front face 702 of the display lens 700 and thus does not reflect light out of the front face 702 but can reflect light back into the display lens 700.

In addition to being angled relative to the front face 702, the angled left side edge 712 also angles inward going from the bottom side edge 710 to the top side edge 718 at an angle Φ relative to left side edge 714. In some embodiments, angle Φ can be approximately ten degrees or in some embodiments, in the range of approximately five degrees to approximately twelve degrees. Other angles are possible. Thus, angled left side edge 712 is disposed at a compound angle that allows light coming from bottom side edge 710 generally directed toward top side edge 718 to be reflected out the left side edge portion 704 of the front face 702.

Likewise, angled right side edge 716 mirrors angled left side edge 712 and is disposed at a compound angle that allows light coming from bottom side edge 710 generally directed toward top side edge 718 to be reflected out the right side edge portion 708 of the front face 702.

Angled top side edge 718 reflects light out of the top edge portion 706 of the front face 702. As shown in FIG. 7C, the angled top side edge 718 is angled relative to the front face 702 as indicated by angle θ. In some embodiments, angle θ can be approximately forty-five degrees or in some embodiments, in the range of approximately thirty degrees to approximately sixty degrees. Other angles are possible.

Figure 8:
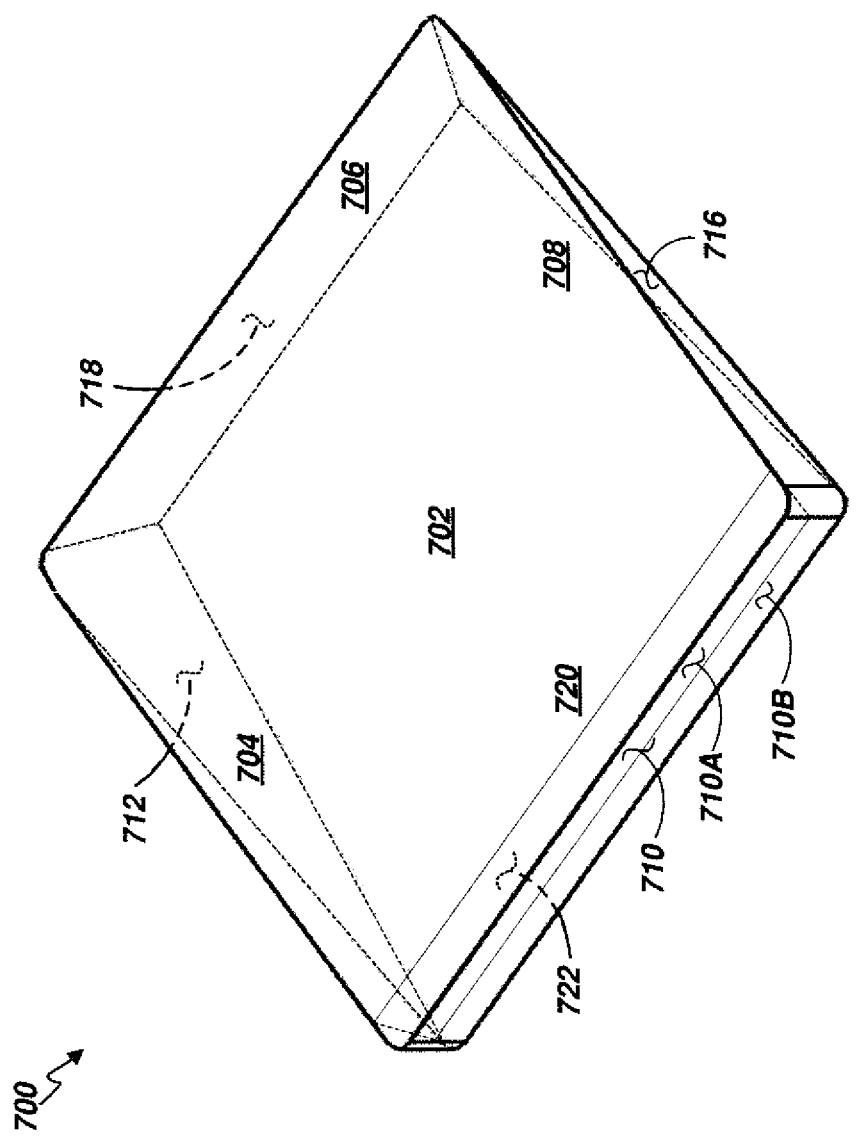
FIG. 8 illustrates an isometric view depicting the example display lens of FIGS. 7A to 7C according to embodiments of the invention.

To reflect light out of the bottom edge portion 720, embodiments of the invention provide an angled internal interface surface 722 as shown in FIGS. 7B, 7C, and 8. Bottom side edge 710 is bisected horizontally into an upper portion 710A and a lower portion 710B. Light incident on lower portion 710B passes into the display lens 700 to be reflected out of the front face 702 by angled left side edge 712, angled right side edge 716, and angled top side edge 718 as described above. Light incident on upper portion 710A, however, is reflected out of bottom edge portion 720 of the front face 702 by angled internal interface surface 722. In some embodiments, angled internal interface surface 722 can be formed by a reflective film disposed between upper portion 710A and the rest of display lens 700 on an angle ε. In some embodiments, angle ε can be approximately forty-five degrees or in some embodiments, in the range of approximately thirty degrees to approximately sixty degrees. Other angles are possible. Alternatively, upper portion 710A can be formed from a clear material that has an index of refraction that is different from that of the clear material used to form the rest of display lens 700. Alternatively, display lens 700 can be chamfered along the top of bottom side edge 710 so that light incident in the chamfer is reflected out from the front face 702 of the display lens 700.

In some embodiments, the positions of the upper portion 710A and the lower portion 7108 can be reversed so that light incident on the upper portion 710A is passed into the display lens 700 to be reflected out of the front face 702 by angled left side edge 712, angled right side edge 716, and angled top side edge 718 as described above. In this reversed embodiment, light incident on the lower portion 710B is reflected out of bottom edge portion 720 of the front face 702 by an angled internal interface surface formed in a manner analogous to the formation of angled internal interface surface 722 described above.

Figure 9:
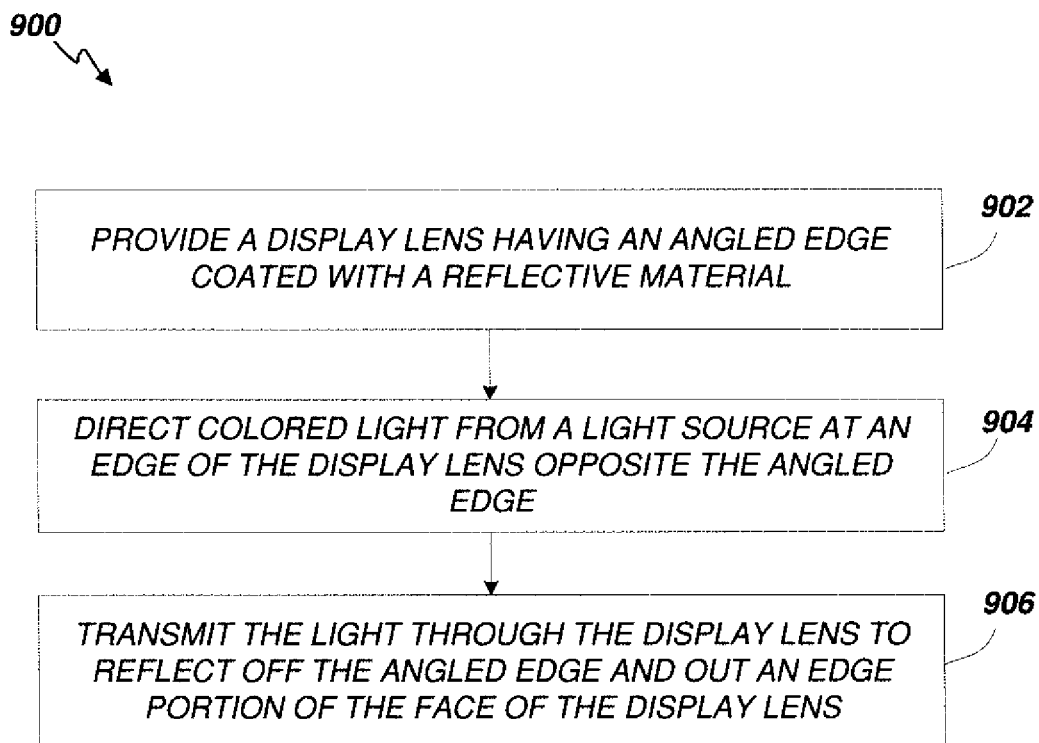
FIG. 9 illustrates a flowchart depicting an example method of illuminating an edge portion of a face of a display lens according to embodiments of the invention.

Turning now to FIG. 9, an example method 900 of illuminating one or more edge portions of a display lens according to embodiments of the invention is illustrated in a flowchart. The example method 900 includes providing a display lens having an angled edge coated with a reflective material (902), directing light from a light source at an edge of the display lens opposite the angled edge (904), and transmitting the light through the display lens to reflect off the angled edge and out an edge portion of the face of the display lens (906). In some embodiments, the light source can be embodied as a light source operable to emit two or more different colors of light. The light can be steady or flashing. The color and duration can be selected by a processor under the control of a program adapted to cause the light source to emit a selected color of light corresponding to a status of data being displayed through the lens display. For example, in some embodiments, the color and duration of the light can be selected based upon information (e.g., numerical values such as blood glucose level) indicating, for example, an urgent condition such as a blood glucose level exceeding a critical high threshold (e.g., hyperglycemic) value or dropping below a critical low threshold (e.g., hypoglycemic) value. Different colors and flashing patterns can be used to indicate different threshold value crossings or statuses. For example, solid red light can be used to indicate that a displayed blood glucose level of 300 mg/dl is dangerously high, red flashing light can be used to indicate a displayed blood glucose level of 600 mg/dl is precariously high. Other colors, flash rates/patterns can be used to indicate the displayed value is within an acceptable or desired range. For example, a solid green light can be used to indicate a displayed blood glucose level between 70 mg/dl and 130 mg/dl is safe.

Numerous embodiments are described in this disclosure, and are presented for illustrative purposes only. The described embodiments are not, and are not intended to be, limiting in any sense. The invention is widely applicable to numerous embodiments, as is readily apparent from the disclosure. One of ordinary skill in the art will recognize that the disclosed embodiments may be practiced with various modifications and alterations, such as structural, logical, software, and electrical modifications. Although particular features of the disclosed embodiments may be described with reference to one or more particular drawings, it should be understood that such features are not limited to usage in the one or more particular embodiments or drawings, unless expressly specified otherwise.

This disclosure is neither a literal description of all embodiments nor a listing of features of the invention that must be present in all embodiments.

The Title (set forth at the beginning of the first page of this disclosure) is not to be taken as limiting in any way as to the scope of the disclosed embodiments.

The term "product" means any machine, manufacture, and/or composition of matter as contemplated by 35 U.S.C. § 101, unless expressly specified otherwise.

Each process (whether called a method, class behavior, algorithm, or otherwise) inherently includes one or more steps, and therefore all references to a "step" or "steps" of a process have an inherent antecedent basis in the mere recitation of the term 'process' or a like term. Accordingly, any reference in a claim to a 'step' or 'steps' of a process has sufficient antecedent basis.

When an ordinal number (such as "first", "second", "third" and so on) is used as an adjective before a term, that ordinal number is used (unless expressly specified otherwise) merely to indicate a particular feature, such as to distinguish that particular feature from another feature that is described by the same term or by a similar term. For example, a "first widget" may be so named merely to distinguish it from, e.g., a "second widget". Thus, the mere usage of the ordinal numbers "first" and "second" before the term "widget" does not indicate any other relationship between the two widgets, and likewise does not indicate any other characteristics of either or both widgets. For example, the mere usage of the ordinal numbers "first" and "second" before the term "widget" (1) does not indicate that either widget comes before or after any other in order or location; (2) does not indicate that either widget occurs or acts before or after any other in time; and (3) does not indicate that either widget ranks above or below any other, as in importance or quality. In addition, the mere usage of ordinal numbers does not define a numerical limit to the features identified with the ordinal numbers. For example, the mere usage of the ordinal numbers "first" and "second" before the term "widget" does not indicate that there must be no more than two widgets.

When a single device, component, structure, or article is described herein, more than one device, component, structure or article (whether or not they cooperate) may alternatively be used in place of the single device, component or article that is described. Accordingly, the functionality that is described as being possessed by a device may alternatively be possessed by more than one device, component or article (whether or not they cooperate).

Similarly, where more than one device, component, structure, or article is described herein (whether or not they cooperate), a single device, component, structure, or article may alternatively be used in place of the more than one device, component, structure, or article that is described. For example, a plurality of computer-based devices may be substituted with a single computer-based device. Accordingly, the various functionality that is described as being possessed by more than one device, component, structure, or article may alternatively be possessed by a single device, component, structure, or article.

The functionality and/or the features of a single device that is described may be alternatively embodied by one or more other devices that are described but are not explicitly described as having such functionality and/or features. Thus, other embodiments need not include the described device itself, but rather can include the one or more other devices which would, in those other embodiments, have such functionality/features.

Devices that are in communication with each other need not be in continuous communication with each other, unless expressly specified otherwise. On the contrary, such devices need only transmit to each other as necessary or desirable, and may actually refrain from exchanging data most of the time. For example, a machine in communication with another machine via the Internet may not transmit data to the other machine for weeks at a time. In addition, devices that are in communication with each other may communicate directly or indirectly through one or more intermediaries.

A description of an embodiment with several components or features does not imply that all or even any of such components and/or features are required. On the contrary, a variety of optional components are described to illustrate the wide variety of possible embodiments of the invention. Unless otherwise specified explicitly, no component and/or feature is essential or required.

Further, although process steps, algorithms or the like may be described in a sequential order, such processes may be configured to work in different orders. In other words, any sequence or order of steps that may be explicitly described does not necessarily indicate a requirement that the steps be performed in that order. The steps of processes described herein may be performed in any order practical. Further, some steps may be performed simultaneously despite being described or implied as occurring non-simultaneously (e.g., because one step is described after the other step). Moreover, the illustration of a process by its depiction in a drawing does not imply that the illustrated process is exclusive of other variations and modifications thereto, and does not imply that the illustrated process or any of its steps are necessary to the invention, and does not imply that the illustrated process is preferred.

Although a process may be described as including a plurality of steps, that does not indicate that all or even any of the steps are essential or required. Various other embodiments within the scope of the invention include other processes that omit some or all of the described steps. Unless otherwise specified explicitly, no step is essential or required.

Although a product may be described as including a plurality of components, aspects, qualities, characteristics and/or features, that does not indicate that all of the plurality are essential or required. Various other embodiments within the scope of the invention include other products that omit some or all of the described plurality.

An enumerated list of items (which may or may not be numbered) does not imply that any or all of the items are mutually exclusive, unless expressly specified otherwise. Likewise, an enumerated list of items (which may or may not be numbered) does not imply that any or all of the items are comprehensive of any category, unless expressly specified otherwise. For example, the enumerated list "a computer, a laptop, a PDA" does not imply that any or all of the three items of that list are mutually exclusive and does not imply that any or all of the three items of that list are comprehensive of any category.

Headings of sections provided in this disclosure are for convenience only, and are not to be taken as limiting the disclosure in any way.

"Determining" something can be performed in a variety of manners and therefore the term "determining" (and like terms) includes calculating, computing, deriving, looking up (e.g., in a table, database or data structure), ascertaining, recognizing, and the like.

A "display" as that term is used herein is an area that conveys information to a viewer. The information may be dynamic, in which case, an LCD, LED, CRT, Digital Light Processing (DLP), rear projection, front projection, or the like may be used to form the display.

This disclosure may refer to a "control system", application, or program. A control system, application, or program, as that term is used herein, may be a computer processor coupled with an operating system, device drivers, and appropriate programs (collectively "software") with instructions to provide the functionality described for the control system. The software is stored in an associated memory device (sometimes referred to as a computer readable medium). While it is contemplated that an appropriately programmed general purpose computer or computing device may be used, it is also contemplated that hard-wired circuitry or custom hardware (e.g., an application specific integrated circuit (ASIC)) may be used in place of, or in combination with, software instructions for implementation of the processes of various embodiments. Thus, embodiments are not limited to any specific combination of hardware and software.

A "processor" means any one or more microprocessors, Central Processing Unit (CPU) devices, computing devices, microcontrollers, digital signal processors, or like devices. Example processors are the INTEL PENTIUM or AMD ATHLON processors.

It will be readily apparent that the various methods and algorithms described herein may be implemented by a control system and/or the instructions of the software may be designed to carry out the processes of the methods and algorithms described herein.

It will be readily apparent that the various methods and algorithms described herein may be implemented by, e.g., appropriately programmed general purpose computers and computing devices. Typically a processor (e.g., one or more microprocessors) will receive instructions from a memory or like device, and execute those instructions, thereby performing one or more processes defined by those instructions. Further, programs that implement such methods and algorithms may be stored and transmitted using a variety of media (e.g., computer readable media) in a number of manners. In some embodiments, hard-wired circuitry or custom hardware may be used in place of, or in combination with, software instructions for implementation of the processes of various embodiments. Thus, embodiments are not limited to any specific combination of hardware and software. Accordingly, a description of a process likewise describes at least one apparatus for performing the process, and likewise describes at least one computer-readable medium and/or memory for performing the process. The apparatus that performs the process can include components and devices (e.g., a processor, input and output devices) appropriate to perform the process. A computer-readable medium can store program elements appropriate to perform the method.

This disclosure provides, to one of ordinary skill in the art, an enabling description of several embodiments of the invention. Some of these embodiments may not be claimed herein, but may nevertheless be claimed in one or more continuing applications that claim the benefit of priority of this application. Applicant may intend to file additional applications to pursue patents for subject matter that has been disclosed and enabled but not claimed herein.

The foregoing description discloses only example embodiments of the invention. Modifications of the above disclosed apparatus and methods which fall within the scope of the invention will be readily apparent to those of ordinary skill in the art. For example, although the examples discussed above are illustrated for the healthcare and/or consumer electronics market, embodiments of the invention can be implemented for other markets.

Accordingly, while the invention has been disclosed in connection with example embodiments thereof, it should be understood that other embodiments may fall within the scope of the invention, as defined by the following claims.

What is claimed is:

1. A method of illuminating an edge portion of a display, the method comprising:
providing a display lens having a face surface, an angled first edge, and two side edges adjacent the angled first edge each having a compound angle configured to reflect light out of a respective side edge portion of the face surface;
directing light from a light source at a second edge of the display lens opposite the angled first edge; and transmitting the light through the display lens to reflect off at least the angled first edge and out at least one edge portion of the face surface of the display lens.

2. The method of claim 1, wherein the providing a display lens includes providing the display lens with the angled first and two side edges each having a reflective coating.

3. The method of claim 1, wherein the providing a display lens includes providing the display lens with the second edge bisected into two portions, wherein:
a first portion allows some light to pass through the display lens to be reflected by the angled first edge, and
a second portion reflects some light out of the face of the display lens.

4. The method of claim 1 wherein the directing light from a light source includes providing colored light.

5. The method of claim 4 wherein the providing colored light includes providing colored light corresponding to a status of information displayed on the display.

6. The method of claim 5 wherein the providing colored light corresponding to the status of information displayed on the display includes:
providing a first color if the value of the information displayed on the display reaches a certain threshold; and
providing a second color different from the first color if the value of the information displayed on the display falls below a certain threshold.

7. A display lens comprising a transparent lens having four edges and a face surface, wherein:
a first edge includes an angle relative to the face surface configured to reflect light in the lens out of the face surface; and
a second edge disposed opposite the first edge configured to reflect light incident on the second edge out of the face surface.

8. The display lens of claim 7 wherein the first edge includes a reflective coating.

9. The display lens of claim 7 wherein the second edge includes an angle relative to the face surface configured to allow light to enter into the lens.

10. The display lens of claim 7 wherein a third edge disposed adjacent the second edge includes a compound angle relative to the face surface configured to reflect light in the lens out of the face surface.

11. The display lens of claim 10 wherein a fourth edge disposed adjacent the second edge and opposite the third edge includes a compound angle relative to the face surface configured to reflect light in the lens out of the face surface.

12. The display lens of claim 11 wherein the third and fourth edges include a reflective coating.

13. The display lens of claim 7 wherein the second edge is bisected into a first portion with an angle relative to the face surface configured to allow light to enter into the lens and a second portion configured to reflect light incident on the second portion out of the face surface.

14. An analyte monitoring device comprising:
an electronic display including a display lens that includes first, second, third, and fourth edges and a face surface surrounded by the first, second, third, and fourth edges; and
a light source disposed adjacent the display lens and configured to illuminate the second edge of the display lens, wherein:
at least two edges of the first, second, third, and fourth edges each includes an angle or compound angle relative to the face surface configured to reflect light in the display lens out a respective edge portion of the face surface.

15. The analyte monitoring device of claim 14 wherein the first edge of the display lens includes a reflective coating.

16. The analyte monitoring device of claim 14 wherein the second edge is disposed opposite the first edge and includes an angle relative to the face surface configured to allow light from the light source to enter into the display lens.

17. The analyte monitoring device of claim 16 wherein:
the third edge of the display lens is disposed adjacent the second edge and includes a compound angle relative to the face surface configured to reflect light in the lens out of a third edge portion the face surface, and
the fourth edge of the display lens is disposed adjacent the second edge and opposite the third edge and includes a compound angle relative to the face surface configured to reflect light in the lens out of a fourth edge portion the face surface.

18. The analyte monitoring device of claim 17 wherein the third and fourth edges of the display lens include a reflective coating.

19. The analyte monitoring device of claim 14 further including a processor operative to display information on the electronic display and to control the light source to select a light color corresponding to a status of the information.

20. The analyte monitoring device of claim 17 wherein the second edge is bisected into a first portion with the angle relative to the face surface configured to allow light to enter into the display lens and a second portion adapted to reflect light incident on the second portion out of a second edge portion of the face surface of the display lens.

* * * * *